United States Patent [19]

Tarrson et al.

[11] 4,162,688
[45] Jul. 31, 1979

[54] MEDICATING FLOSS DISPENSER AND METHOD OF APPLYING MEDICATION TO HUMAN TEETH

[75] Inventors: Emanuel B. Tarrson, Chicago; Stevan Tisma, Niles, both of Ill.

[73] Assignee: John O. Butler Company, Chicago, Ill.

[21] Appl. No.: 831,150

[22] Filed: Sep. 7, 1977

[51] Int. Cl.² .............................................. A61C 15/00
[52] U.S. Cl. ................................................. 132/92 A
[58] Field of Search ................... 132/89, 91, 92 A, 93; 225/44, 46, 51, 63, 24; 242/129.8, 118.4, 137.1

[56] References Cited
U.S. PATENT DOCUMENTS

| | | | |
|---|---|---|---|
| 3,147,897 | 9/1964 | Ratte et al. | 225/24 |
| 3,746,017 | 7/1973 | Casselman | 132/92 A |
| 3,830,247 | 8/1974 | Kaphalakos | 132/90 |
| 3,902,510 | 9/1975 | Roth | 132/92 A |
| 4,034,770 | 7/1977 | Trecker | 132/90 |

*Primary Examiner*—G. E. McNeill
*Attorney, Agent, or Firm*—Laff, Whitesel & Rockman

[57] ABSTRACT

A floss holder includes a bobbin of preferably unwaxed floss which feeds through a chamber containing a medication, such as fluoride. While in the chamber, the floss passes through a number of bearing surfaces for squeezing the medication into the floss without disturbing the lay of the fibers in the floss. After leaving the medication chamber, the floss passes out of the floss holder, over a stand-off prong and to a cutter. A clutch may be provided in the bobbin to maintain a floss tension throughout the medication chamber.

7 Claims, 5 Drawing Figures

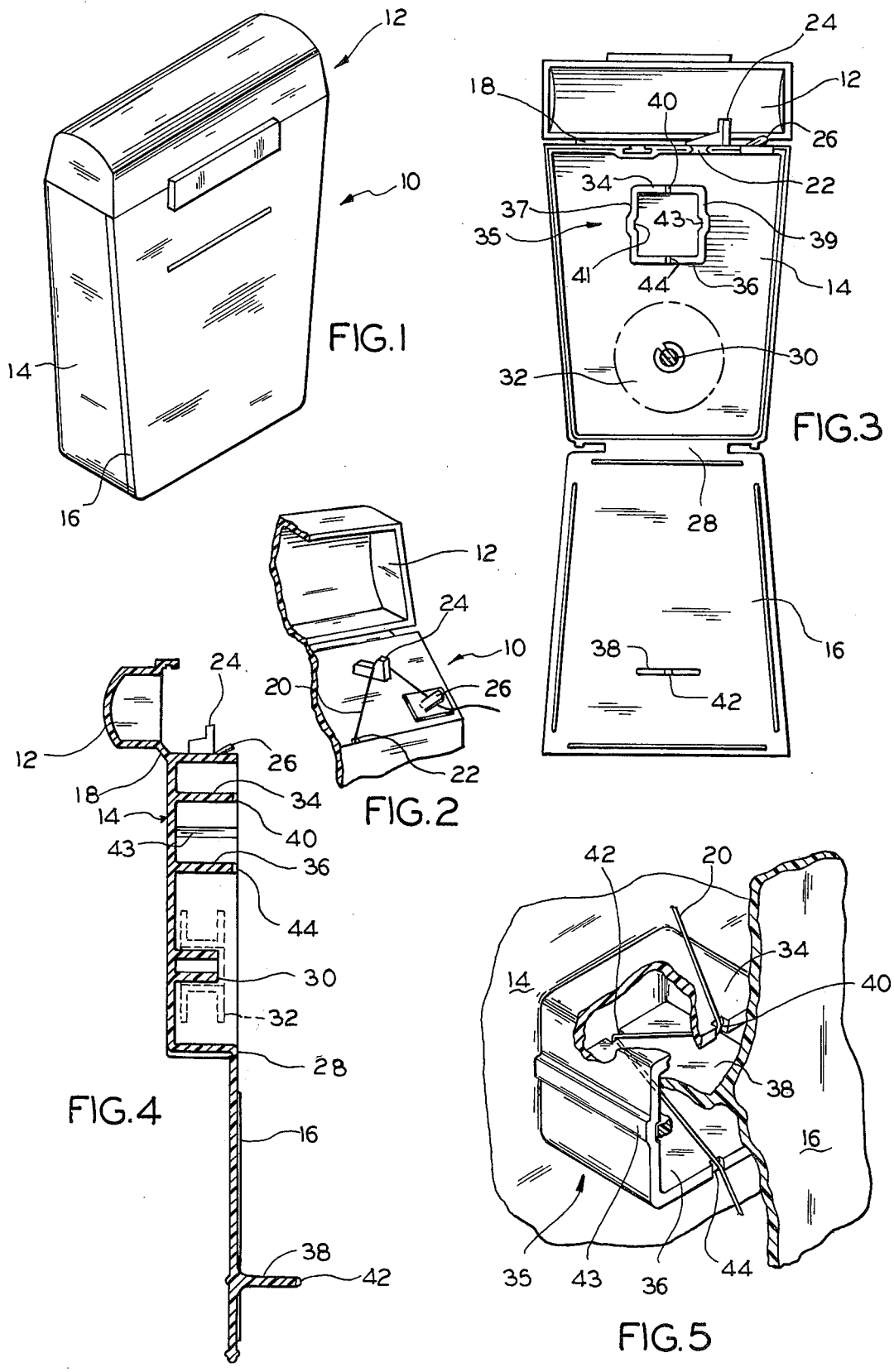

MEDICATING FLOSS DISPENSER AND METHOD OF APPLYING MEDICATION TO HUMAN TEETH

This invention relates to floss holders and more particularly to means for impregnating floss with a medication.

Fluorides are exemplary of a medication which is applied to teeth to help prevent decay. Originally, fluoride was only applied by a doctor or dentist. However, at the present, the fluoride is also applied to the teeth through self-help by being mixed into toothpaste or drinking water. One of the problems which is encountered with such self-help techniques is that the fluoride is not always applied to the hard-to-reach places such as under the bridges or between teeth, for example.

Dental flossing is one of the methods which people use to reach into these places. The advantages of fluorides applied by floss have been known for a long period of time. However, heretofore, there have not been any satisfactory ways of using the flossing as part of a process for working the fluoride into these places.

One of the problems of so working fluoride into these out-of-the-way places with floss is that there is a better result if the fluoride is in a wet or fresh condition when applied. Thus, a floss which was previously wet and then dried does not give satisfactory fluoride treatment. When efforts were used to pull the floss directly from a chamber filled with a fluid or gel, the strand was rather messy and tended to be objectional to the user. If efforts were made to better impregnate the floss with a fluid or a gel, it sometimes caused the fibers of the floss to become combed out or otherwise disturbed, which mechanically weakened the floss. Accordingly, there is a need for new and improved, self-help methods of applying fluoride in the hard-to-reach parts of the mouth without ever leaving the floss in a messy or weakened condition.

An object of this invention is to apply fresh fluoride to dental floss at a time which is immediately before the floss is to be used. In this connection, an object is to provide means for and methods of impregnating and saturating floss with a liquid or gel immediately before the floss is to be used. Here, an object is to accomplish these ends without leaving the floss either messy or mechanically weak.

Another object is to provide new and improved means for and methods of applying medication to human teeth and more particularly to hard-to-reach places between teeth, under bridges, and the like. Here, an object is to so apply medication through self-help means, whereby the user automatically medicates his teeth each time that he performs a function which he habitually does every day.

Yet another object of the invention is to provide floss holders which automatically accomplish the foregoing objects responsive to the withdrawal of floss from the holder.

In keeping with an aspect of this invention, these and other objects are accomplished by a floss holder which includes a bobbin of preferably unwaxed floss. The floss pulled from the bobbin is fed through a chamber containing a medication, such as fluoride, for example. While it is in the chamber, the floss passes through a number of bearing surfaces for squeezing the medication into and saturating the floss without disturbing the lay of fibers in the floss. After leaving the medication chamber, the floss passes out of the floss holder. A bobbin clutch may be built into the holder in order to maintain a predetermined floss tension throughout the medication chamber.

The nature of a preferred embodiment may be understood from the attached drawings, in which:

FIG. 1 is a perspective view of the outside of the floss holder;

FIG. 2 is a perspective view of the floss holding and cutting part of the floss holder;

FIG. 3 is a plan view of the floss holder; as it is manufactured and before it is loaded with either floss or medication;

FIG. 4 is a side elevation view of the floss holder in the same unloaded condition; and FIG. 5 is a perspective view of a medication chamber in the floss holder, which shows how the floss passes through a series of bearing surfaces that squeeze the medication into the floss.

In the description which follows, it will sometimes be convenient to refer to a use of "living hinges," which are thin areas that enable integrally formed plastic parts to fold along a preferred crease line. However, a use of any particular form of a hinge depends upon many things, such as the cost of production, for example. Therefore, the invention should be viewed as broad enough to include any kind of a hinge. Or, separate parts may be snapped or welded together, without any hinges.

As best seen in FIG. 1, the floss holder, as actually used by the consumer, comprises a housing 10 and a cover 12. The housing 10 has two parts 14,16 which snap together to form a container for both the floss and the medication. If desired, the cover 12 may be attached to one of these housing parts 14 by means of a living or other convenient form of hinge, at 18.

When the cover 12 is opened (FIG. 2), the top of the housing 10 is seen as having a strand of dental floss 20 emerging from a hole 22, passing over a stand-off prong 24 and under a detent 26 for cutting and capturing the cut end of the floss. The stand-off prong 24 holds the floss at an elevated position so that it is easy to grasp between the thumb and index finger. Thus, to use the floss, strand 20 is gripped and pulled away from the cutting detent 26. Any suitable length of floss is pulled out of hole 22, led over the stand-off prong 24, and then anchored and cut under the cutting detent 26.

The construction details of the inventive floss holder are seen in FIGS. 3 and 4. In greater detail, the entire structure is preferably molded from plastic, as a single unit. There are three major portions 12,14,16 in this molded structure which preferably fold on living or other hinges 18,28 to form the box or floss holder, as seen in FIG. 1. One of the parts, 14, includes an upstanding post 30 which is shaped, proportioned, and formed to receive a hub of a bobbin 32. Preferably, this bobbin contains a length of unwaxed dental floss. A clutch may be imposed between the hub and the post in order to restrain the bobbin rotation and thereby establish and maintain a predetermined tension in the floss. Any suitable clutch may be used, such as those shown in the following applications, all entitled "Thread Storage and Dispensing System," and assigned to the assignee of this invention: Ser. No. 678,138, filed Apr. 19, 1976, Tarrson and Tisma, inventors; Ser. No. 743,693, filed Nov. 22, 1976, Tisma, inventor; and Ser. No. 833,441, filed Sept. 15, 1977, Tarrson and Tisma, inventors.

An open-topped box 35, including two upstanding bulkheads 34,36, is integrally formed on one of the housing parts 14, and one upstanding bulkhead 38 is integrally formed on the other housing part 16. The bulkheads 34,36 are opposing sides of the open top, generally rectangular box 35 which is used for containing and dispensing a medication, which is loaded therein when the bobbin 32 is installed over the post 30. The other two sides of this box 37,39 are shaped to form spaced parallel guide rails 41,43. When the housing parts are snapped together, the box 35 forms a medicine dispensing chamber.

When the two housing parts 14,16 are snapped together or folded along the living or other suitable hinge 28, the bulkhead 38 is interposed into the guide rails 41,43 and slipped into position approximately midway between the two bulkheads 34,36. A bearing surface 40,42,44 is formed on the side of each of the upstanding bulkheads 34,36 and 38, respectively, which is the side that is remote from the housing part that supports it. Each of these bearings is a cut or notch which is dimensioned to receive and squeeze the strand of floss 20 without disturbing the lay of the floss fibers.

Therefore, to load the medicine and the floss into the floss holder, it is only necessary to pull the floss strand 20 from the bobbin, pass it over bearing surfaces 40,42,44 and out the hole 22. When the housing part 16 folds along hinge 28 and snaps into housing part 14, the bearing surface 44 bears down upon the floss 20. At this time, the floss travels over a relatively long, V-shaped path from bearing 44, over bearing 42, and through the bearing 40 (FIG. 6). As it so travels, the floss must pass through the medical dispensing chamber formed by the box or container 33–36. The chamber may be filled with any suitable fluid or gel. Therefore, as the floss is pulled through each of the bearing surfaces, it is squeezed. After it leaves the bearing surface, it is relaxed. This squeezing and relaxing of the floss insures that the floss becomes completely saturated with the medicine, when it leaves the chamber 33,36.

An advantage of this arrangement is that the floss drawn from the hole 22 is freshly saturated with a liquid or gel. Therefore, when the floss is used in the mouth, a fresh liquid or gel is transferred to the user's teeth.

Those who are skilled in the art will readily perceive how various changes and modifications may be made in the inventive structure and method. Therefore, the appended claims should be construed to cover all equivalents falling within the true scope and spirit of the invention.

We claim:

1. A medicating dental floss dispenser comprising a holder having a bobbin rotatably mounted therein, a medicine chamber located in said holder and positioned adjacent said bobbin, said medicine chamber including a plurality of bearing surfaces which are distributed throughout said chamber to cause the floss to follow a relatively long path through the medicine chamber, said bearing surfaces alternately squeezing and relaxing said floss without disturbing the lay of the fibers so that the floss becomes saturated with the medicine while it moves through said chamber, means for drawing said floss from said bobbin, through said medicine chamber, and out a port in said holder and means for maintaining a back tension in said floss while it travels from said bobbin, through said holder, and to the outside of said holder.

2. The dispenser of claim 1 wherein said holder comprises a unitary molded plastic housing having at least two parts separated by hinge means, one of said housing parts including means for supporting said bobbin and an internal container including at least two upstanding bulkheads for forming opposing walls of said medicine chamber, another of said housing parts including at least one additional upstanding bulkhead positioned within the medicine chamber and between said two bulkheads when said two housing parts are brought together with pivoting of said hinge, and said bearing surfaces being means formed on sides of said upstanding bulkheads which are remote from the housing part which supports the bulkhead, whereby floss threaded through said bearing surfaces travels over a relatively long V-shaped path through said medicine chamber.

3. The dispenser of claim 1 and stand-off means formed on said holder adjacent said port in said holder so that it is easy to pick up the floss as it leaves said stand-off means, and floss-cutting and anchoring means adjacent said stand-off means, whereby floss emerging from said port passes over said stand-off means and through said cutting means.

4. A method for treating human teeth with a fluoride medication comprising the steps of:
 (a) storing a supply of unwaxed dental floss adjacent a medicine chamber containing a fluoride inside a floss holder;
 (b) drawing said floss from said supply, against a back tension, and through the fluoride in said medicine chamber to the outside of said floss holder while alternately squeezing and relaxing said floss while in said chamber; and
 (c) cutting and anchoring the cut end of said floss on the outside of said floss holder.

5. The method of claim 4 wherein step (b) includes the added step of leading said floss through a plurality of bearing surfaces disposed to form a relatively long path through said medicine chamber, said bearing surfaces alternately squeezing and releasing of said floss to cause it to soak up said fluoride.

6. The method of claim 6 and the added step of supporting said floss on said holder in a stand-off condition adjacent said cutting and anchoring point, whereby said floss is easy to pick up.

7. The method of claim 6 and the added step of forming said floss holder from a single integral plastic part which folds and snaps together.

* * * * *

UNITED STATES PATENT AND TRADEMARK OFFICE
CERTIFICATE OF CORRECTION

PATENT NO.  : 4,162,688
DATED       : July 31, 1979
INVENTOR(S) : Emanuel B. Tarrson and Stevan Tisma It is certified that error appears in the above—identified patent and that said Letters Patent are hereby corrected as shown below:

Column 4, line 50, "The method of claim 6" should read

--The method of claim 5--

Signed and Sealed this

Thirteenth Day of November 1979

[SEAL]

Attest:

RUTH C. MASON
Attesting Officer

LUTRELLE F. PARKER
Acting Commissioner of Patents and Trademarks